United States Patent
Persen et al.

(10) Patent No.: US 7,801,611 B2
(45) Date of Patent: Sep. 21, 2010

(54) SYSTEM AND METHOD FOR PROVIDING COMMUNICATIONS BETWEEN A PHYSICALLY SECURE PROGRAMMER AND AN EXTERNAL DEVICE USING A CELLULAR NETWORK

(75) Inventors: Kenneth H. Persen, Maple Grove, MN (US); Vineel Vallapureddy, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 656 days.

(21) Appl. No.: 10/859,649

(22) Filed: Jun. 3, 2004

(65) Prior Publication Data
US 2005/0288736 A1 Dec. 29, 2005

(51) Int. Cl.
*A61N 1/00* (2006.01)
(52) U.S. Cl. ...................................................... 607/31
(58) Field of Classification Search .................... 607/31; 370/328, 332, 334, 915
See application file for complete search history.

(56) References Cited

U.S. PATENT DOCUMENTS

| | | | |
|---|---|---|---|
| 5,720,770 | A | 2/1998 | Nappholz et al. |
| 6,024,699 | A | 2/2000 | Surwit et al. |
| 6,083,248 | A | 7/2000 | Thompson |
| 6,171,256 | B1 | 1/2001 | Joo et al. |
| 6,327,501 | B1 | 12/2001 | Levine et al. |
| 6,336,903 | B1 | 1/2002 | Bardy |
| 6,368,284 | B1 | 4/2002 | Bardy |
| 6,386,882 | B1 * | 5/2002 | Linberg ................. 434/262 |
| 6,398,728 | B1 | 6/2002 | Bardy |
| 6,411,840 | B1 | 6/2002 | Bardy |
| 6,416,471 | B1 * | 7/2002 | Kumar et al. ........... 600/300 |
| 6,434,568 | B1 * | 8/2002 | Bowman-Amuah ..... 707/103 R |
| 6,440,066 | B1 | 8/2002 | Bardy |
| 6,442,433 | B1 | 8/2002 | Linberg |
| 6,480,745 | B2 * | 11/2002 | Nelson et al. ............. 607/60 |

(Continued)

FOREIGN PATENT DOCUMENTS

WO WO 01/93756 12/2001

(Continued)

OTHER PUBLICATIONS

W. R. Stevens, "TCP/IP Illustrated," vol. 1, Chs. 1-3, Addison Wesley Longman, Inc., Reading, MA (1994).

(Continued)

*Primary Examiner*—George Manuel
(74) *Attorney, Agent, or Firm*—Pauly, DeVries Smith & Deffner, L.L.C.

(57) ABSTRACT

A system and method for providing communications between a physically secure programmer and an external device using a cellular network is described. A set of uniquely identifying credentials is securely maintained on a programmer configured to interface with an implantable medical device. A transient connection is automatically established between the programmer and a security server over a cellular network. The credentials are registered with the security server and an operational status is assigned to the programmer following examination of the credentials against a security roster maintained on the security server. The operational status of the programmer is confirmed and a data exchange session is conducted over the cellular network between the programmer and at least one external system subsequent to the confirmation.

37 Claims, 11 Drawing Sheets

U.S. PATENT DOCUMENTS

| | | | |
|---|---|---|---|
| 6,641,533 B2 * | 11/2003 | Causey et al. | 600/300 |
| 6,648,823 B2 | 11/2003 | Thompson | |
| 6,827,670 B1 | 12/2004 | Stark et al. | |
| 6,850,252 B1 * | 2/2005 | Hoffberg | 715/716 |
| 7,027,872 B2 | 4/2006 | Thompson | |
| 7,065,409 B2 * | 6/2006 | Mazar | 607/60 |
| 7,155,290 B2 | 12/2006 | Von Arx et al. | |
| 7,181,017 B1 * | 2/2007 | Nagel et al. | 380/282 |
| 7,228,182 B2 * | 6/2007 | Healy et al. | 607/60 |
| 7,270,633 B1 * | 9/2007 | Goscha et al. | 600/300 |
| 7,272,383 B2 * | 9/2007 | Jung | 455/411 |
| 7,475,245 B1 | 1/2009 | Healy et al. | |
| 2001/0051787 A1 * | 12/2001 | Haller et al. | 604/66 |
| 2002/0010679 A1 * | 1/2002 | Felsher | 705/51 |
| 2002/0045920 A1 | 4/2002 | Thompson | |
| 2002/0052539 A1 * | 5/2002 | Haller et al. | 600/300 |
| 2002/0082665 A1 * | 6/2002 | Haller et al. | 607/60 |
| 2002/0123673 A1 * | 9/2002 | Webb et al. | 600/300 |
| 2003/0174066 A1 | 9/2003 | Goetz et al. | |
| 2005/0203582 A1 * | 9/2005 | Healy et al. | 607/31 |
| 2005/0204134 A1 | 9/2005 | Von Arx et al. | |
| 2006/0219776 A1 * | 10/2006 | Finn | 235/380 |
| 2007/0053513 A1 * | 3/2007 | Hoffberg | 380/201 |

FOREIGN PATENT DOCUMENTS

| | | |
|---|---|---|
| WO | WO 03/006107 | 1/2003 |
| WO | WO 03/066159 | 8/2003 |
| WO | WO 2004/041352 | 5/2004 |

OTHER PUBLICATIONS

Health Insurance Portability And Accountability Act of 1996, Pub. L. No. 104-191, 110 Stat. 1936 (1996).

E. Hammond, "National Committee on Vital And Health Statistics, Subcommittee On Health Data Needs, Standards And Security," http://www.ncvhs.hhs.gov/970211t3.htm, pp. 1-4 (Feb. 11, 1997).

Security And Electronics Signature Standards, 63 Fed. Reg. 155 (proposed Aug. 12, 1998).

W. Diffie, "The First Ten Years Of Public-Key Cryptography," Proceedings of the IEEE, vol. 76, No. 5, pp. 560-577 (May 1988).

File history for related EP patent application No. 05759751.0, corresponding to U.S. Appl. No. 10/859,649, issued Feb. 24, 2010, "A System for Communication Between a Programmer and an External Device Over a Cellular Network" (39 pages).

File History in co-pending Japanese patent application No. 2007-515591, corresponding to U.S. Appl. No. 10/859,649, "Providing Communications Between a Physically Secure Programmer and an External Device Using a Cellular Network", filed Jun. 3, 2005 (23 pages).

International Preliminary Report on Patentability for International application No. PCT/US2005/019482, corresponding to U.S. Appl. No. 10/859,649, mailed Dec. 14, 2006 (7 pages).

Written Opinion and International Search Report for International application No. PCT/US2005/019482,, corresponding to U.S. Appl. No. 10/859,649, mailed Oct. 13, 2005 (7 pages).

Model 2920 Programmer Recorder Monitor Operator's Manual, Jul. 2000 (24 pages).

* cited by examiner

200

230

260

SYSTEM AND METHOD FOR PROVIDING COMMUNICATIONS BETWEEN A PHYSICALLY SECURE PROGRAMMER AND AN EXTERNAL DEVICE USING A CELLULAR NETWORK

FIELD OF THE INVENTION

The invention relates in general to cellular network communications and, specifically, to a system and method for providing communications between a physically secure programmer and an external device using a cellular network.

BACKGROUND OF THE INVENTION

In general, implantable medical devices (IMDs) provide in situ therapy delivery, such as cardiac pacing and defibrillation, neural stimulation, and drug dispensing, and physiological data collection. IMDs are controlled and monitored through external programmers, programmer recorder monitors, repeaters, and equivalent devices, hereafter simply "programmers." Conventionally, programmers exchange parametric and physiological data through inductive telemetry with the IMDs. Although limited to a range of about six inches, inductive telemetry facilitates safe and non-invasive data exchange. Moreover, patient consent and confidentiality are assured through the use of a wand placed in physical contact with the patient's body.

More recently, radio frequency (RF) telemetry has been adopted for IMD-programmer communication with longer ranges and higher bandwidth data exchange. The sweeping scope of recent medical information privacy laws, such as the Health Insurance Portability and Accountability Act (HIPAA) and the European Privacy Directive, may affect patient privacy on IMDs with longer transmission ranges, such as provided through RF telemetry, and other unsecured data interfaces providing sensitive information exchange under conditions that could allow eavesdropping, interception or interference. As a result, RF telemetry requires additional safeguards to ensure that each programmer is properly authenticated prior to and during data exchange, such as described in commonly-assigned U.S. patent application Ser. No. 10/800,806, filed Mar. 15, 2004, pending, and U.S. patent application Ser. No. 10/801,150, filed Mar. 15, 2004, pending, the disclosures of which are incorporated by reference.

Until recently, programmers primarily functioned as standalone medical devices to store, view and process downloaded physiological data as patient histories and to reprogram IMDs with revised operational settings uploaded as parametric values. Limited data exchange with other programmers and external devices, such as personal computers, was historically provided through data diskettes storing the data in a proprietary format. Lately, though, programmers have increasingly included integrated external communication channels, including low speed serial modem connections and high speed network connections, which can provide interconnectivity to a centralized server respectively over standard telephone lines and wide area networks, such as the Internet.

The ability to interface programmers to IMDs at longer ranges through RF telemetry and to connect programmers to external devices outside the control of the health care practitioner has created the need to ensure the physical security of programmers, in addition to providing transmission security. For instance, a rogue programmer, such as obtained through theft, could be used to maliciously reprogram an IMD using RF telemetry or to surreptitiously download a patient history. Similarly, a rogue programmer could also be used to upload corrupt parametric values or fabricated patient histories onto the centralized server, which could adversely affect those health care practitioners relying on the stored data for consideration in forming therapy decisions.

Disabling the operation of a programmer from unauthorized use provides a highly effective physical security solution. However, safeguarding the physical security of programmers must be balanced against ease of use. Programmers are typically used in a clinical or hospital setting shared by numerous individuals, including physicians, nurses and technical staff, and physical safeguards, such as provided with a key switch, can prove inconvenient and unworkable. Similarly, soft safeguards, such as provided through user passwords, can be easily bypassed or compromised through user carelessness or inadvertence. On the other hand, external safeguards transfer the responsibility for physical security to a third party by requiring pre-authorization from a centralized server using a modem or network connection before enabling the programmer. External safeguards are transparent with negligible impact on ease of use, yet always cannot be assured unless the recipient of an unauthorized programmer chooses to use the modem or network connection to obtain pre-authorization and thereby risk detection.

U.S. Pat. No. 6,648,823, issued Nov. 18, 2003 to Thompson and U.S. Pat. No. 6,442,433, issued Aug. 27, 2002 to Linberg both describe a programmer that is interfaced to a remote expert data center. The programmer provides a high speed communications scheme that includes a wireless Internet connection. The expert data center is Web-based and interacts with the IMDs through the programmer to remotely exchange clinically significant information and to effect real time parametric and operational changes. Thompson describes accessing a patient and device information database, identifying devices or components that are out of specification, and notifying a clinician or the patient of out of specification items. Linberg describes remotely diagnosing, maintaining, upgrading, performance tracking, tuning, and adjusting a programmer from a remote location. However, neither Thompson nor Linberg describe providing remote registration of a programmer over a cellular network coupled with the integrated disablement of a programmer if attempts at credentialing fail.

Therefore, there is a need for an approach to providing cellular network-based communication between a programmer and an external system integrated with distributed safeguards to protect programmer physical security. Preferably, such an approach would be maintained on a central database of registered programmers that must be accessed and confirmed as legitimate before enabling the programmer for operations. Such an approach would further be capable of interfacing to a plurality of external systems for collaborative exchanging of data relative to the IMD and patient care.

SUMMARY OF THE INVENTION

The physical security of a programmer is assured by integrating the registration of credentials that uniquely identify the programmer with a security server over a cellular network with a power up sequence. The security credentials are provided to the security server over a high speed cellular connection that is automatically established transparently to the user during programmer power up. The security server compares the credentials to a secure roster of programmer credentials, which can list legitimate programmers or untrusted programmers. If confirmed as legitimate, the security server signals the programmer to enable operational status. Otherwise, if untrusted, the security server signals the programmer to disable operational status, thereby preventing unauthorized usage.

An embodiment provides a system and method for providing communications between a physically secure programmer and an external device using a cellular network. A set of uniquely identifying credentials are securely maintained on a programmer configured to interface with an implantable medical device. A transient connection is automatically established between the programmer and a security server over a cellular network. The credentials is registered with the security server and an operational status is assigned to the programmer following examination of the credentials against a security roster maintained on the security server. The operational status of the programmer is confirmed and a data exchange session is conducted over the cellular network between the programmer and at least one external system subsequent to the confirmation.

Still other embodiments of the invention will become readily apparent to those skilled in the art from the following detailed description, wherein are described embodiments of the invention by way of illustrating the best mode contemplated for carrying out the invention. As will be realized, the invention is capable of other and different embodiments and its several details are capable of modifications in various obvious respects, all without departing from the spirit and the scope of the invention. Accordingly, the drawings and detailed description are to be regarded as illustrative in nature and not as restrictive.

DETAILED DESCRIPTION

Implantable Medical Device

Figure 1:
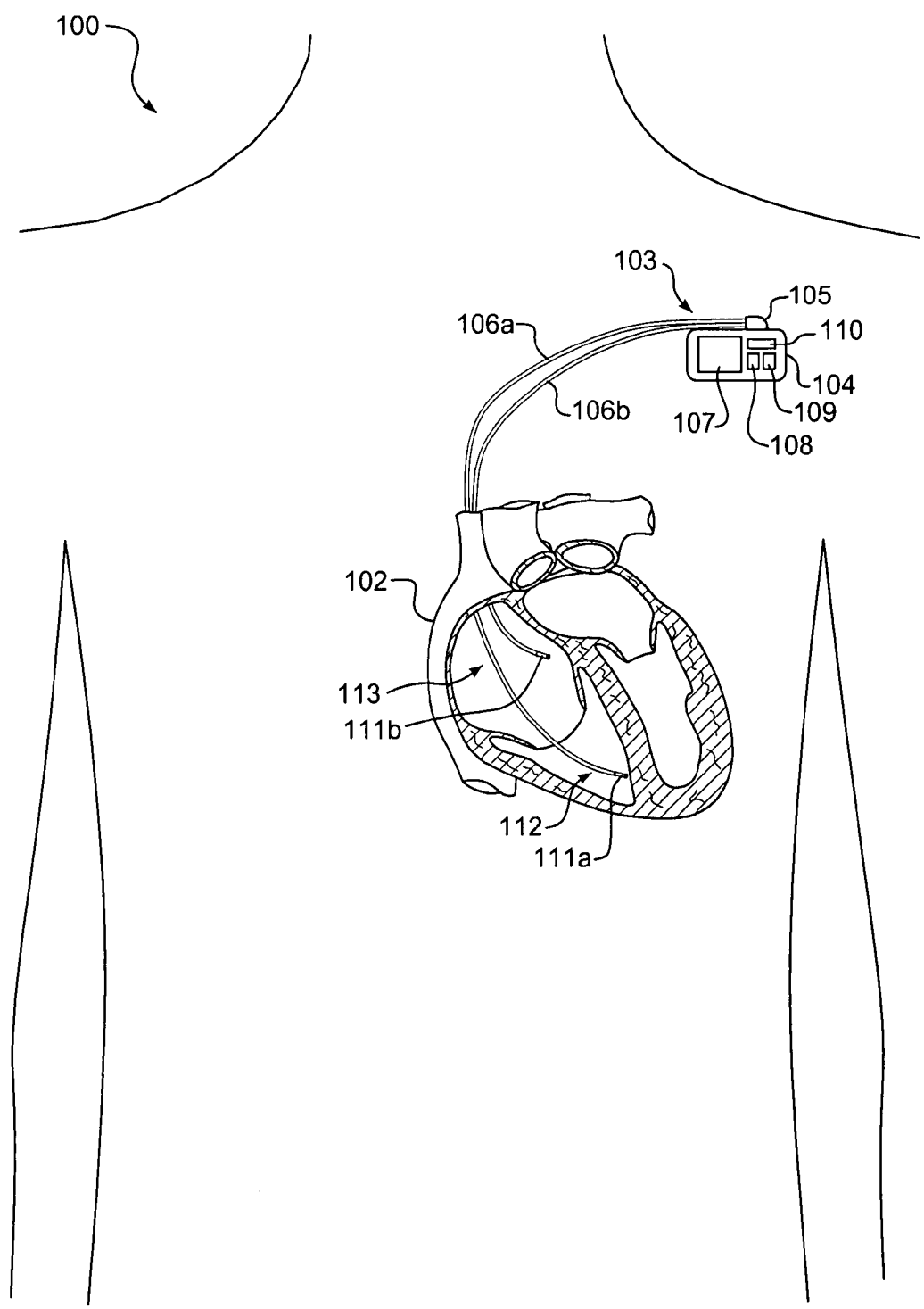
FIG. 1 is a block diagram showing, by way of example, an implantable medical device monitoring physiological parameters of a patient.

FIG. 1 is a block diagram 100 showing, by way of example, an implantable medical device (IMD) 103 monitoring physiological parameters of a patient, in accordance with an embodiment of the invention. By way of example, an implantable cardiac device, such as an implantable pulse generator or implantable cardioverter defibrillator is described. Although presented with reference to implantable cardiac monitoring and therapy delivery, IMDs 103 also include neural stimulation, drug dispensing, and other implantable, as well as external, monitoring and therapy delivery devices.

The IMD 103 is surgically implanted in the chest or abdomen of a patient and consists generally of a housing 104 and terminal block 105. The IMD 103 is coupled to a set of leads 106a-b at the terminal block 105. During surgery, the leads 106a-b are threaded through a vein and placed into the heart 102 with the distal tips of each lead 106a-b positioned in direct contact with tissue inside the heart 102.

The housing 104 contains a battery 107, control circuitry 108, memory 109, and telemetry circuitry 110. The battery 107 provides a finite power source for the IMD components. The control circuitry 108 samples and processes raw data signals and includes signal filters and amplifiers, memory and a microprocessor-based controller. The memory 109 includes a memory store in which raw physiological signals can be stored for later retrieval and analysis. The telemetry circuitry 110 provides an interface between the IMD 103 and external devices, such as an external programmer, programmer recorder monitor, repeater, and equivalent devices (not shown), hereafter simply "programmer." The telemetry circuitry 110 enables operating parameters to be non-invasively programmed into the memory 109 through an external device in telemetric communication with the IMD 103. The telemetry circuitry 110 also allows patient history information collected by the IMD 103 and transiently stored in the memory 109 to be sent to the external device for processing and analysis.

The IMD 103 is in direct electrical communication with the heart 102 through electrodes 111a-b positioned on the distal tips of each lead 106a-b. By way of example, the set of leads 106a-b can include a right ventricular electrode 111a and a right atrial electrode 111b. The right ventricular electrode 111a is preferably placed in the right ventricular apex 112 of the heart 102 and the right atrial electrodes 111b is preferably placed in the right atrial chamber 113 of the heart 102. The electrodes 111a-b enable the IMD 103 to directly collect raw physiological measures, preferably through millivolt measurements. Other configurations and arrangements of leads and electrodes, including the use of single and multiple leads arrays and single and multiple electrodes, can be used, as would be recognized by one skilled in the art.

In the described embodiment, the IMD 103 can be implemented as part of cardiac pacemakers used for managing bradycardia, implantable cardioverter defibrillators used for treating tachycardia, and other types of implantable cardiovascular monitors and therapeutic devices used for monitoring and treating structural problems of the heart, such as congestive heart failure, as well as rhythm problems. Examples of cardiac pacemakers suitable for use in the described embodiment include the Pulsar Max II, Discovery, and Discovery II pacing systems, sold by Guidant Corporation, St. Paul, Minn. An example of an implantable cardioverter defibrillator suitable for use in the described embodiment includes the Contak Renewal cardiac resynchronization therapy defibrillator, also sold by Guidant Corporation, St. Paul, Minn.

On a regular basis, the raw physiological signals stored in the memory 109 are retrieved as part of a patient history. In addition, operational settings are retrieved as parametric values. By way of example, a programmer can be used to retrieve the raw physiological signals. However, any form of programmer, repeater, interrogator, recorder, monitor, or transceiver suitable for communicating with IMD 103 could be used. As necessary, revised operational settings can also be stored by the programmer to reprogram the IMD 103.

For short range data exchange, the IMD 103 communicates with the programmer or repeater through inductive telemetry signals exchanged through a wand placed over the location of the IMD 103. Programming or interrogating instructions are sent to the IMD 103 and the stored raw physiological signals are downloaded into the programmer. In a further embodiment, the IMD 103 communicates with an external device capable of long range telemetry, such as a radio frequency (RF) programmer, repeater or other wireless computing device. Other types of data interfaces are possible. Prior to initiating the long range data exchange session, patient/clinician authentication is performed through secure crypto key retrieval and long range telemetry is transacted through secure data exchange, such as described in commonly-assigned U.S. patent application Ser. No. 10/800,806, filed Mar. 15, 2004, pending, and U.S. patent application Ser. No. 10/801,150, filed Mar. 15, 2004, pending, the disclosures of which are incorporated by reference.

In a further embodiment, the IMD 103 includes a telemetry interlock that limits communication between the IMD 103 and an external device. Patient/clinician authentication is secured through release of the telemetry interlock, which can be used in conjunction with secure crypto key retrieval. The telemetry interlock is released when the external device transmits an ENABLE command to the IMD 103 via short range telemetry, such as described in commonly-assigned U.S. patent application Ser. No. 10/601,763, filed Jun. 23, 2003, pending, the disclosure of which is incorporated by reference.

An example of a programmer with inductive telemetry is the Model 2920 Programmer Recorder Monitor, manufactured by Guidant Corporation, Indianapolis, Ind., which includes the capability to store retrieved raw physiological signals on a removable floppy diskette, known as a patient data diskette. The raw physiological signals can later be electronically transferred using a personal computer or similar processing device. The stored raw physiological signals and operational settings can also be retrieved from the IMD 103 and electronically transferred to via cellular network, as further described below beginning with reference to FIG. 3.

Implantable Medical Device

Figure 2:
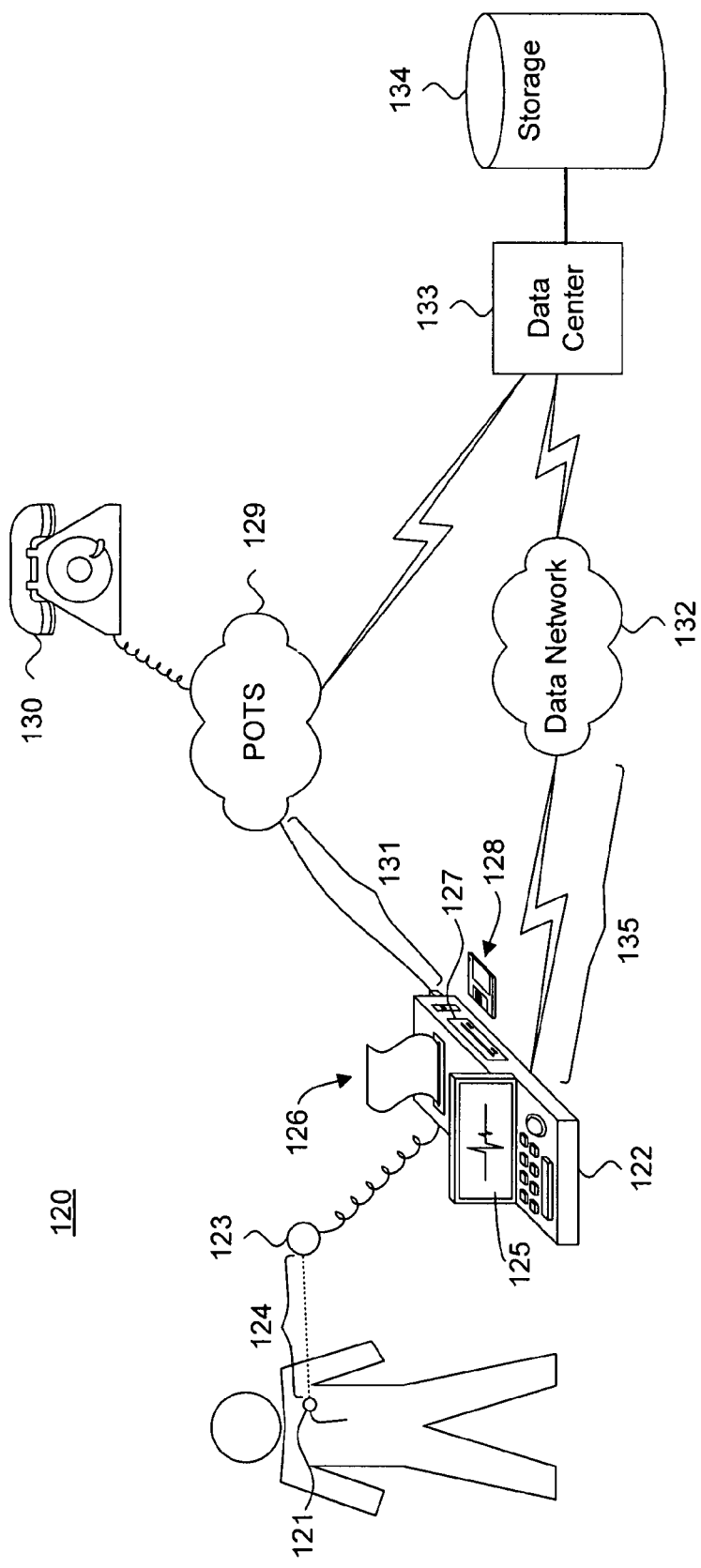
FIG. 2 is a block diagram showing a prior art system for providing communications between a programmer and an external device.

FIG. 2 is a block diagram showing a prior art system 120 for providing communications between a programmer 122 and an external device. During use, the programmer 122 is initially powered up, completes any self-tests and initializes the programmer 122 for IMD interrogation. A wand 123 is placed over the location of an IMD 121, which sends parametric values and patient history data to the programmer 122 over the telemetric link 124. The programmer 122 can store, view and process the downloaded patient histories, such as by using a display screen 125 or printer 126, and can reprogram the IMD 121 with revised operational settings uploaded. The downloaded data can also be transferred one or more external devices, such as a data center 133.

By way of example, the programmer 122 is operatively interfaced to a data center 133 operated on a server coupled to an external storage device 134. The programmer 122 can interface to the data center 133 through several means. First, data, such as parametric values that include operational settings and patient history data that includes physiological measures, can be stored on a patient data diskette 128 using a diskette drive 127 integral to the programmer 122. The patient data diskette 128 can be manually transferred to the data center 133 and read in, provided the data center 133 supports the format used to store the data on the patient data diskette 128.

Alternatively, the data can be electronically transferred over a low speed serial modem connection 131 or via a high speed network connection 135. The low speed serial modem connection 131 allows the programmer 122 to utilize a standard POTS (Plain Old Telephone System) line 129 to access an Internet Service Provider (ISP) (not shown), which transacts a network data exchange session with the data center 133 on behalf of the programmer 122. The low speed serial modem connection 131 provides the convenience of flexibility, but requires a compatible telephone connection and a dialup telephone account with the ISP. Depending upon the hospital, clinic or similar physical environment, compatible telephone connections can be difficult to obtain, particularly where the telephone system is digital and incompatible with conventional analog modems. As well, setting up and configuring the dialup telephone account on the programmer 122 can be an involved and daunting task for technically-challenged users. Furthermore, the programmer 122 must contend with other users of the telephone system, including conventional telephone 130 and other modem users.

The high speed network connection 135 bypasses the ISP and enables the programmer 122 to directly access the data center 133 over a data network 132, such as the Internet. The high speed network connection 135 provides the convenience of high bandwidth data transfer, but requires a compatible network connection, which must generally be provided by the information technology (IT) infrastructure of the hospital, clinic or similar physical environment. In addition, access to the available network may be subject to security controls pertaining to authorized access and to data transfer from within and into the network, such as due to firewalls or Internet filters.

System Overview

Figure 3:
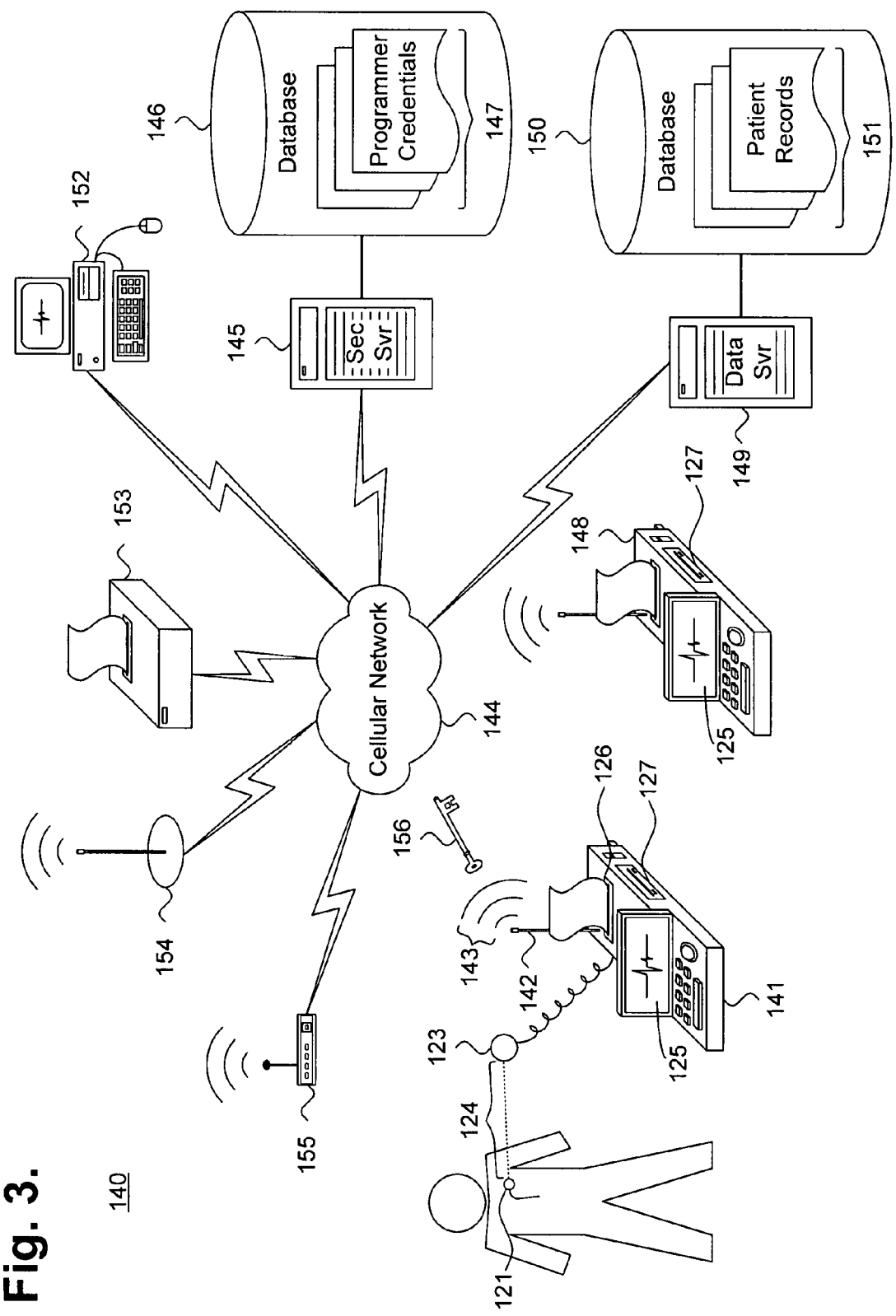
FIG. 3 is a block diagram showing a system for providing communications between a physically secure programmer and an external device using a cellular network, in accordance with an embodiment of the invention.

FIG. 3 is a block diagram showing a system 140 for providing communications between a physically secure programmer 141 and an external device using a cellular network 144, in accordance with an embodiment of the invention. As before, during use, the programmer 141 is initially powered up, completes any self-tests and initializes the programmer 141 for IMD interrogation. However, the power up procedure also transparently registers a credentials 156 uniquely assigned to the programmer 141 with a security server 145 before enabling the programmer 141 for further operation. Thus, following successful registration, a wand 123 is placed over the location of an IMD 121, which sends parametric values and patient history data to the programmer 141 over the telemetric link 124. The programmer 141 can similarly store, view and process the downloaded patient histories, such as by using a display screen 125 or printer 126, and can reprogram the IMD 121 with revised operational settings uploaded. The downloaded data can also be transferred to one or more external devices, such as a data server 149.

As part of the atomic power up procedure, the programmer 141 automatically establishes a connection with a security server 145 over a cellular network 144 to register the credentials 156 uniquely identifying the programmer 141. From a user's standpoint, the connection is transparent and does not require a physical connection to a phone or network jack, account set up and configuration or permissions to gain access and work within a controlled security framework. The programmer 141 includes an integral cellular transceiver 142, which allows the programmer 141 to automatically access the cellular network 144 via a high speed cellular connection 143, as further described below with reference to FIG. 5. Upon establishing the high speed cellular connection 143, the programmer 141 sends the credentials 156 to the security server 145 over a network interface for comparison to a roster of programmer credentials 147 securely maintained in a database 146.

The credentials 156 are securely maintained on the programmer 141. In the described embodiment, the credentials 156 can include the serial number assigned to the programmer 141 at the factory, a security certificate, such as an RSA security certificate, an asymmetric crypto key, or any other form of uniquely assignable credential. The roster 147 lists those credentials 156 assigned to legitimate programmers 141 that are enabled for continued operation by the security server 145. In a further embodiment, the roster 147 lists those credentials 156 assigned to untrusted programmers 141 that are disabled for continued operation by the security server 145. An untrusted programmer 141 includes rogue programmers reported lost or missing or which fail repeatedly fail to complete a mandatory security procedure, such as a user logon sequence. Other types of rogue programmers are possible, wherein operational status is denied by the security server 145.

Upon successful registration, the security server 145 assigns an operational status to the credentialing programmer 141, which confirms the continued operational status of the programmer 141. The data retrieved from the programmer 141 can then be electronically exchanged with a plurality of external devices via the cellular network 144. The programmer 141, cellular network 144 and external devices each implement standard network protocol stacks for exchanging structured packetized data. In the described embodiment, Transmission Control Protocol/Internet Protocol (TCP/IP) compliant network protocol stacks are used, such as described in W. R. Stevens, "TCP/IP Illustrated," Vol. 1, Chs. 1-3, Addison Wesley Longman, Inc., Reading, Mass., (1994), the disclosure of which is incorporated by reference, although other types of network protocol stacks could also be used. The cellular network 144 primarily provides point-to-point connectivity by implementing the link and network layers, while the programmer 141 and the external devices provide end-to-end connectivity by also implementing the link and network layers, plus the transport and application layers, if applicable. In the described embodiment, the cellular network 144 can be CDMA, GSM, GPRS, WCDMA compliant, although other types of cellular networks could also be used.

The external devices non-exclusively include a further programmer 148, the security server 145, data server 149, personal computer 152, network printer 153, external antenna 154, and dedicated repeater 155. The further programmer 148 and dedicated repeater 155 also include an integral cellular transceiver, which allows the further programmer 148 and the dedicated repeater 155 to automatically access the cellular network 144 via a high speed cellular connection. Upon successful registration of both the programmer 141 and the further programmer 148, the data can be cooperatively exchanged and analyzed over the cellular network 144 and each programmer can perform equivalent operations on the data, except for reprogramming the IMD 121, which can only be performed by the immediately IMD-interfaceable programmer 141. The programmer 141 can also cause the further programmer 148 to download and store data on other external devices. The dedicated repeater 155 is assigned to single IMD 121 for a particular patient's exclusive use and only, upon successful registration, only allows data upload and reprogramming settings download on an IMD-specific basis.

The data server 149 maintains a set of patient records 151 in a database 150 in which parametric values and patient history data can be stored. Alternatively, the set of patient records 151 could be maintained in the database 146 managed by the security server 145. Similarly, the data can be exchanged with the personal computer 152 and each of the security server 145, data server 149 and personal computer 152, as applicable, can store, view and process the downloaded patient histories and generate reprogramming parameters for the IMD 121. In addition, the data can be evaluated and matched as quantitative pathophysiological measures against one or more medical conditions, such as described in related, commonly-owned U.S. Pat. No. 6,336,903, to Bardy, issued Jan. 8, 2002; U.S. Pat. No. 6,368,284, to Bardy, issued Apr. 9, 2002; U.S. Pat. No. 6,398,728, to Bardy, issued Jun. 2, 2002; U.S. Pat. No 6,411,840, to Bardy, issued Jun. 25, 2002; and U.S. Pat. No. 6,440,066, to Bardy, issued Aug. 27, 2002, the disclosures of which are incorporated by reference. In a further embodiment, the data can be supplemented with qualitative measures, such as quality of life measures or other semi-quantitative self-assessments of individual patient physical and emotional well being. Non-commercial, non-proprietary standardized quality of life scoring systems are readily available, such as provided by the Duke Activities Status Indicator.

Finally, the network printer 153 and external antenna 154 perform ancillary functions. The network printer 153 allows the programmer 141 to printout the data on a high quality, high volume printer, whereas the external antenna 154 mitigates cellular signal strength dips that can potentially occur within buildings. In the described embodiment, the external antenna 154 is a Pico cell antenna or distributed antenna array, although other forms of supplemental cellular antennas are possible.

Process Flow

Figure 4:
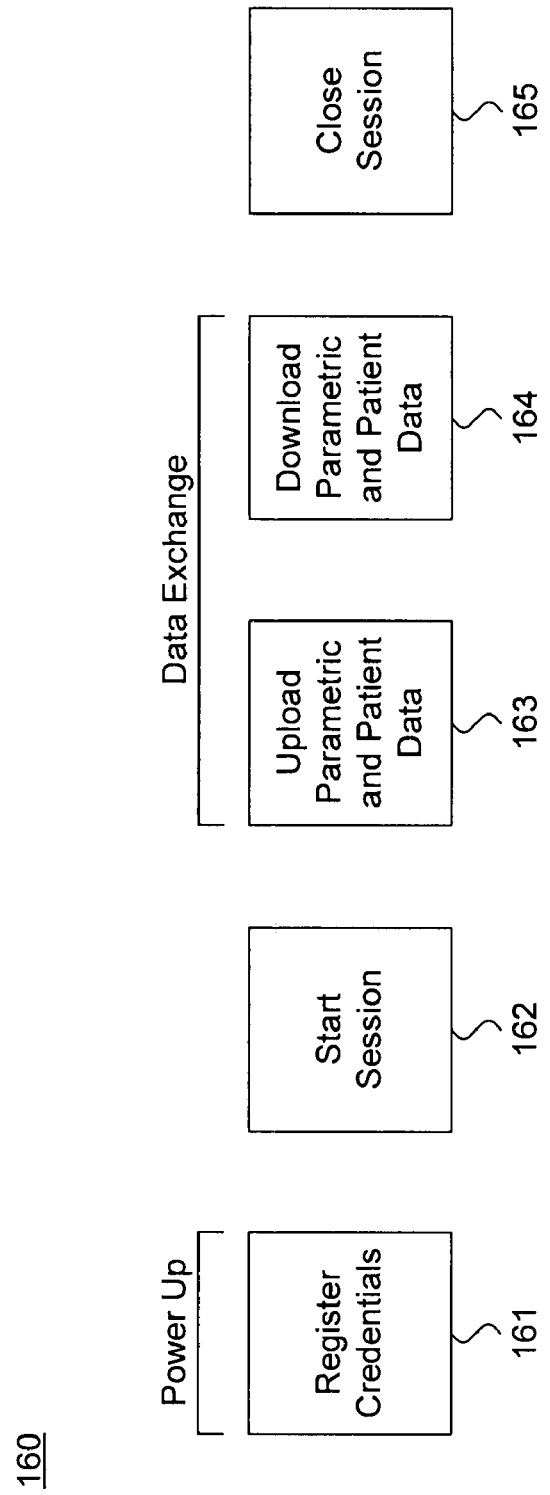
FIG. 4 is a process flow diagram showing cellular network communications as performed by the system of FIG. 3.

FIG. 4 is a process flow diagram showing cellular network communications 160 as performed by the system 140 of FIG. 3. For clarity, the ancillary operations performed by the programmer 141 and external devices, such as data storage, viewing and processing, are omitted. During power up, each programmer 141 registers credentials 156 (operation 161) with a security server 145. A data exchange session is started with the IMD 121 (operation 162) only after successfully confirming the credentials 156 against the roster of programmer credentials 147 maintained by the security server 145. During the data exchange session, parametric values and patient history data is uploaded from and downloaded to the IMD 121 (operations 163 and 164, respectively), after which the data exchange session can be closed (operation 165).

Programmer Schematic

Figure 5:
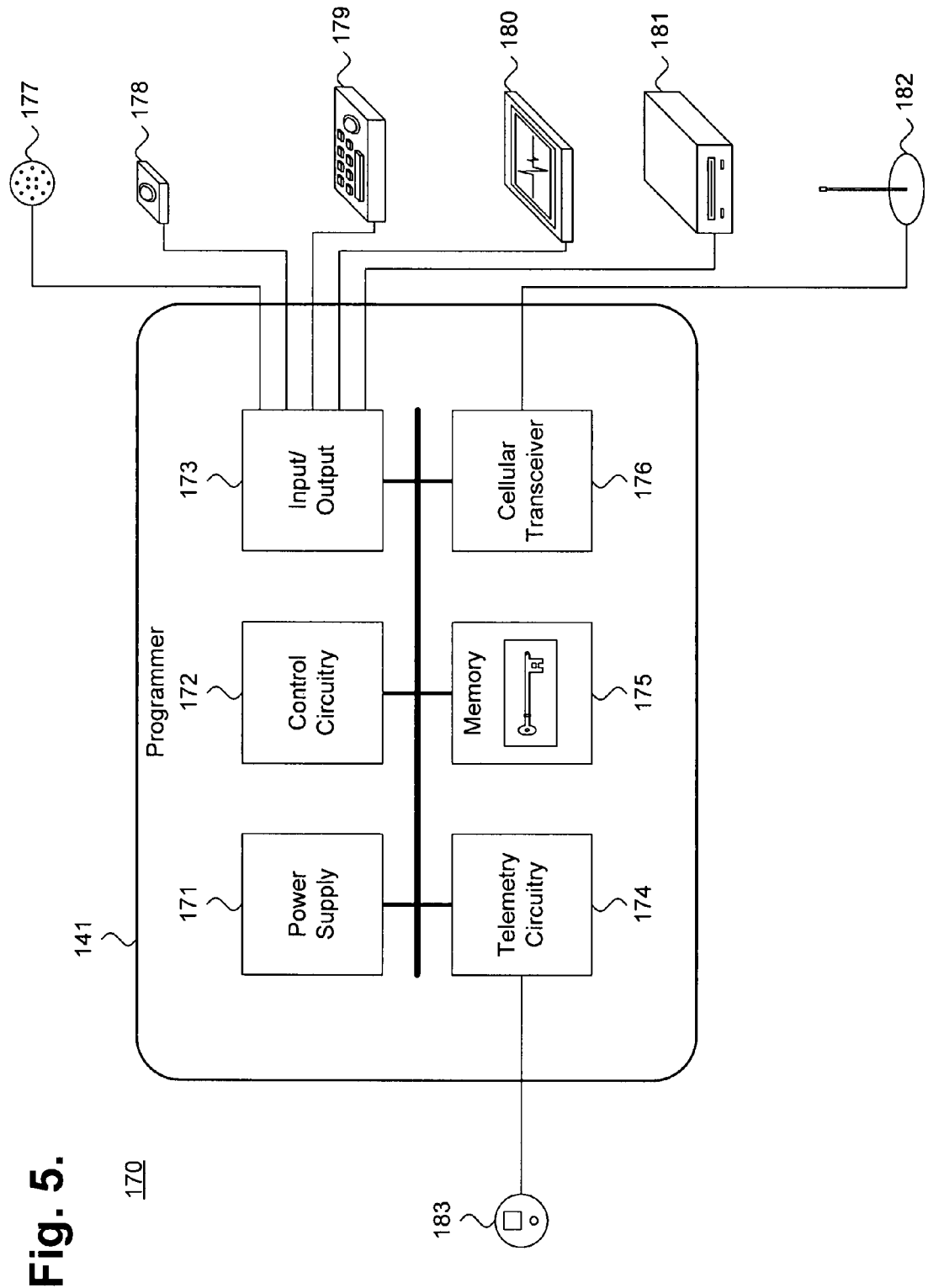
FIG. 5 is a functional schematic diagram showing, by way of example, a programmer configured to communicate using a cellular network, in accordance with an embodiment of the invention.

FIG. 5 is a functional schematic diagram 170 showing, by way of example, a programmer 141 configured to communicate using a cellular network 144, in accordance with an embodiment of the invention. The programmer 141 contains a power supply 171, control circuitry 172, input/output circuitry 173, telemetry circuitry 174, memory 175, and cellular transceiver 176. The power supply 171 provides a power source for the programmer components. The control circuitry 172 processes downloaded parametric values and patient history data and includes signal filters and amplifiers, memory and a microprocessor-based controller. The control circuitry 172 also registers the credentials 156 with the security server 145 and enables the programmer 141 for continued operation following successful confirmation. The input/output circuitry 173 provides an external interface to the user through input/output devices, such as speaker 177, pointing device 178, keyboard 179, display 180, diskette drive 181, and external antenna 182. Other types of input/output devices are possible. The telemetry circuitry 174 provides an interface between the programmer 141 and IMD 121 through a wand 183 and enables operating parameters to be non-invasively programmed into the IMD 103 through telemetric communication. The telemetry circuitry 174 also allows retrieval of patient history information collected and transiently stored by the IMD 121 for processing and analysis. The memory 175 includes a memory store in which downloaded parametric values and patient history data can be stored for later retrieval and analysis by the control circuitry 171 or for transferal to other external devices. Finally, the cellular transceiver 176 enables the programmer 141 to establish a connection over the cellular network 144. In the described embodiment, the cellular transceiver 176 is integrated at the circuit level into the programmer 141. In a further embodiment, the cellular transceiver 176 is provided as a removable PCMCIA-compliant expansion card, such as the Merlin C201 wireless CDMA cellular communications card.

Method Overview

Figure 6:
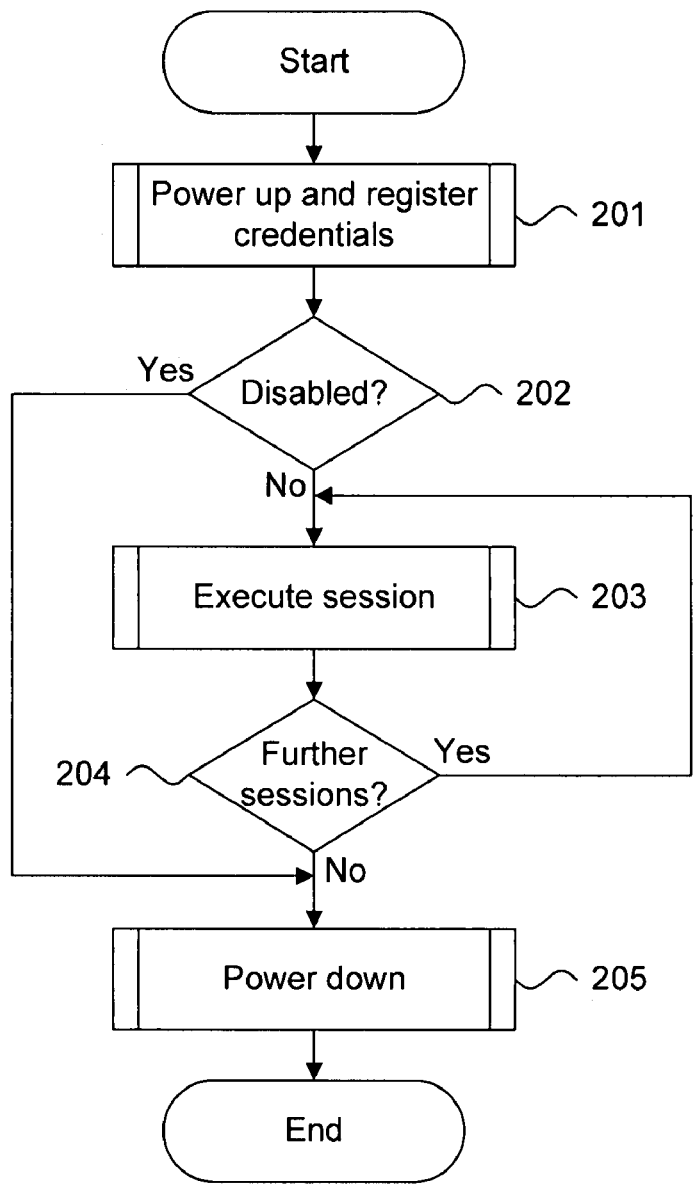
FIG. 6 is a flow diagram showing a method for providing communications between a physically secure programmer and an external device using a cellular network, in accordance with an embodiment of the invention.

FIG. 6 is a flow diagram showing a method 200 for providing communications between a physically secure programmer 141 and an external device using a cellular network 144, in accordance with an embodiment of the invention. The method 200 is described as a sequence of process operations or steps, which can be executed, for instance, by the programmer 121, further programmer 148, dedicated repeater 155, or other components.

Initially, the programmer 141 undergoes a power up, during which the credentials 156 are registered (block 201), as further described below with reference to FIG. 7. Power up and credential registration are completed as an atomic procedure and the continued operation of the programmer 141 is disabled (block 202) if the programmer 141 cannot be confirmed as being legitimate. If confirmed and not disabled (block 202), the programmer 141 can proceed to execute a data exchange session (block 203), as further described below with reference to FIG. 9. Further data exchange sessions can also be executed with the same or other external devices (block 204), after which the programmer 141 undergoes a power down (block 205), as further described below with reference to FIG. 10. The method then terminates.

Power Up and Credential Registration

Figure 7:
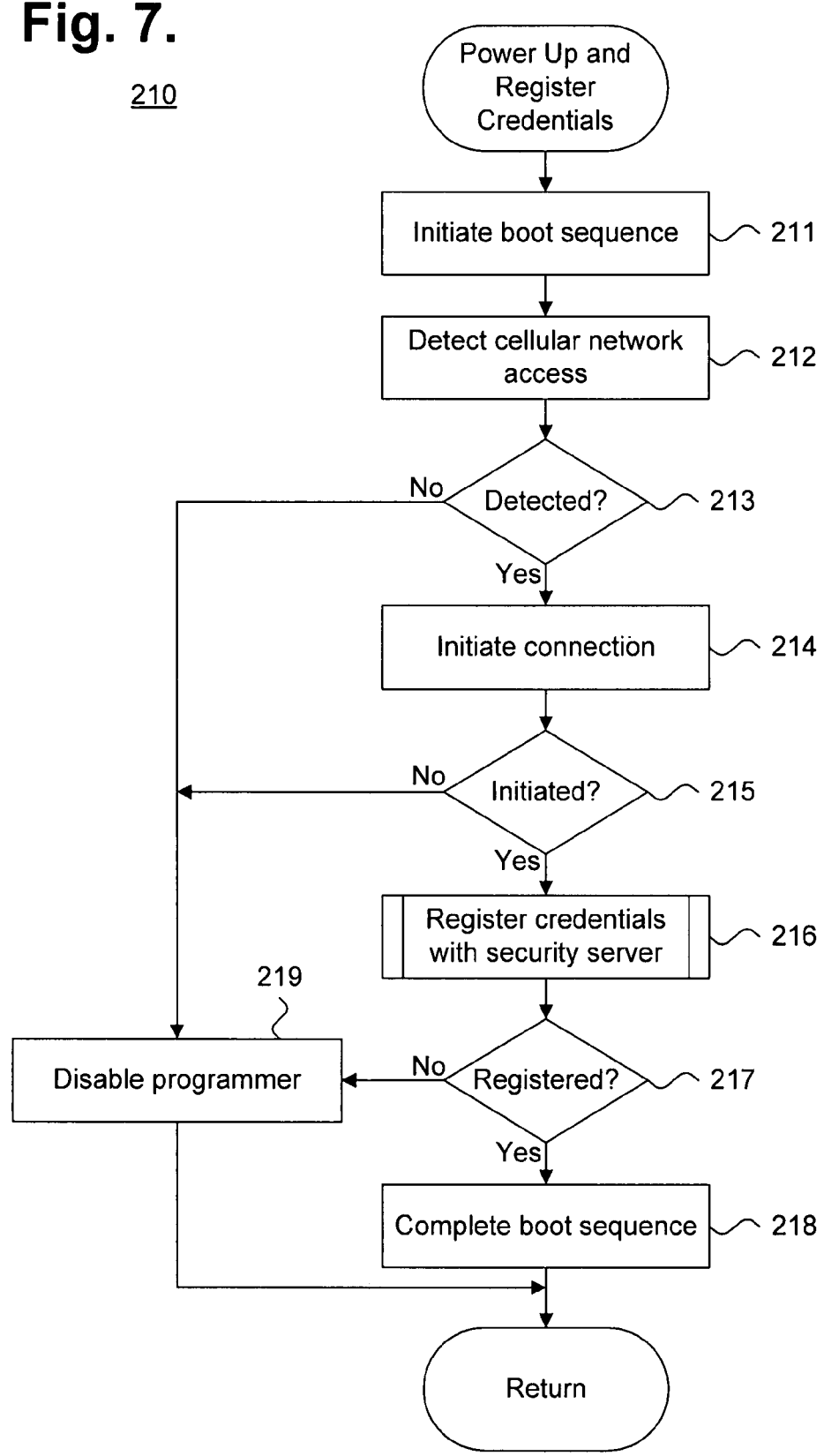
FIG. 7 is a flow diagram showing a routine for powering up and registering credentials for use in the method of FIG. 6.

FIG. 7 is a flow diagram showing a routine 210 for powering up and registering credentials for use in the method 200 of FIG. 6. The purpose of this routine is integrate the power up sequence with the registration of credentials 156 to form an atomic procedure.

The boot sequence of the programmer 141 is initiated (block 211) and the cellular transceiver 176 is accessed to detect cellular network access (block 212). If a cellular network 144 is not detected (block 213), the programmer 141 is disabled from further operation (block 219). Otherwise, a high speed cellular connection 143 is initiated (block 214). If the connection fails (block 215), the programmer 141 is disabled from further operation (block 219). Otherwise, if initiated (block 215), the credentials 156 are registered with the security server 145 (block 216), as further described below with reference to FIG. 8. If registration fails (block 217), the programmer 141 is disabled from further operation (block 219). Otherwise, if registered successfully (block 217), the boot sequence completes and the programmer 141 commences operations (block 218). The routine then returns.

Credential Registration

Figure 8:
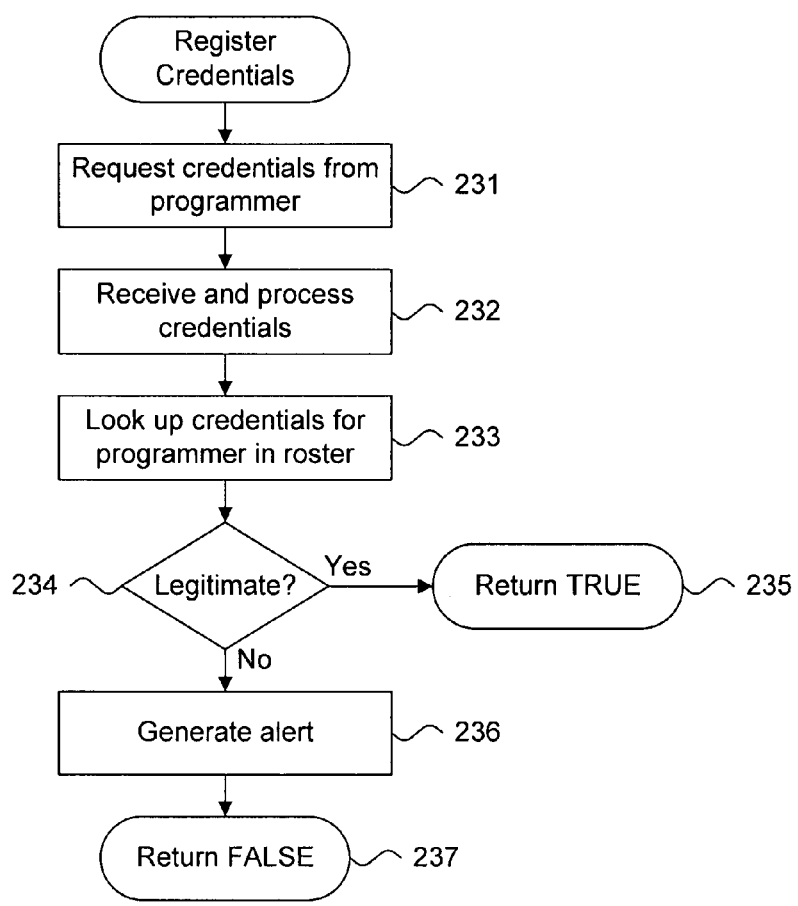
FIG. 8 is a flow diagram showing a routine for registering credentials for use in the routine of FIG. 7.

FIG. 8 is a flow diagram showing a function 230 for registering credentials for use in the routine 210 of FIG. 7. The purpose of this function is register credentials 156 received from an unconfirmed programmer 141 prior to enabling or disabling the programmer 141 from further operation.

Following automatic connection via the cellular network 144, the security server 145 requests the credentials 156 from the unconfirmed programmer 141 (block 231), which are received and processed (block 232). Processing can include parsing a security certificate or decrypting an asymmetric crypto key. The credentials corresponding to the unconfirmed programmer 141 are looked up in the roster 147 (block 233) to determine whether the unconfirmed programmer 141 is legitimate or untrusted. In the described embodiment, the roster 147 lists those credentials 156 assigned to legitimate programmers 141 that are enabled for continued operation by the security server 145. In a further embodiment, the roster 147 lists those credentials 156 assigned to untrusted programmers 141 that are disabled for continued operation by the security server 145. If the unconfirmed programmer 141 is legitimate (block 234), the function returns TRUE flag to signal the programmer 141 as confirmed (block 235). If the unconfirmed programmer 141 is untrusted (block 234), an alert is generated (block 236) for the health care provider or patient and the function returns FALSE flag to signal the programmer 141 as unconfirmed (block 237).

Session Execution

Figure 9:
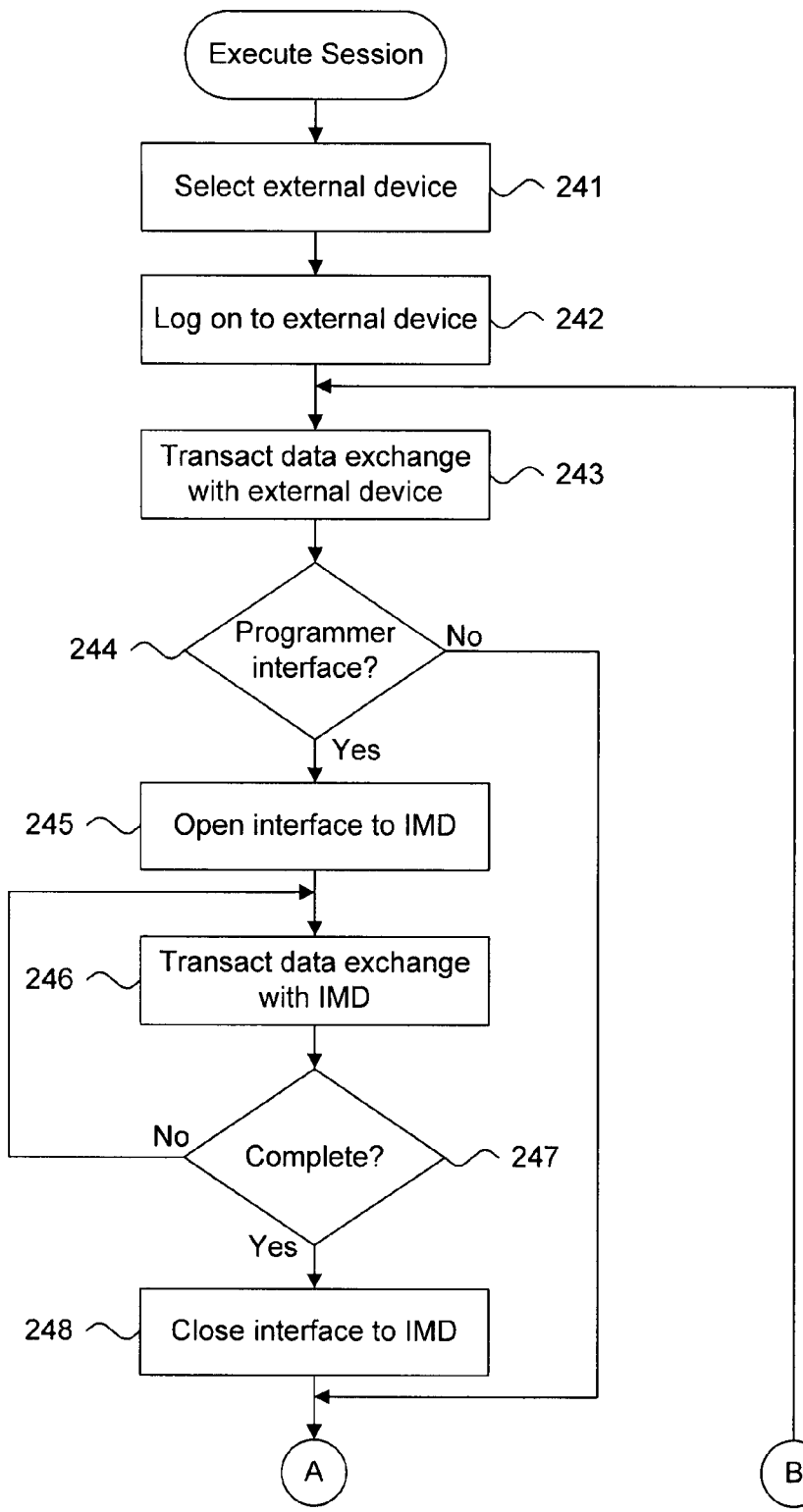
FIG. 9 is a flow diagram showing a routine for executing a session for use in the method of FIG. 6.
Figure 9:
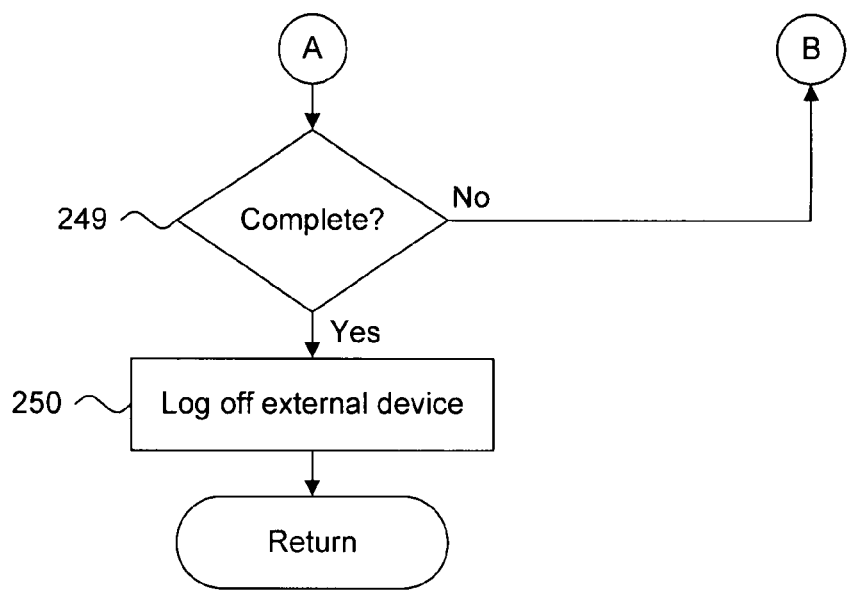

FIG. 9 is a flow diagram showing a routine 240 for executing a session for use in the method 200 of FIG. 6. The purpose of this routine is generically transact a data exchange session between the programmer 141 and one or more external devices.

An external device is first selected (block 241) and, if necessary, the programmer logs on to the external device (block 242). A data exchange is transacted with the external device (block 243). The type of data exchange is dependent upon the type of data being exchanged, the nature of the external device vis-à-vis the programmer 141, the operations performed on the data, and whether the data exchange is one-way, two-way or bi-directional, such as further described above with reference to FIG. 3. In particular, if the programmer 141 is interfacing to a further programmer 148 (block 244), an interface is opened to the IMD 121, such as through inductive telemetry (block 245) and a data exchange is transacted with the IMD 121 (block 246), which can include indirectly interfacing by the further programmer 148 with the IMD 121 through the programmer 141. When the further programmer interfacing is complete (block 247), the interface to the IMD 121 is closed (block 248). Similarly, when the external device interfacing in complete (block 249), if applicable, the programmer 141 logs off the external system (block 250). The routine then returns.

Power Down

Figure 10:
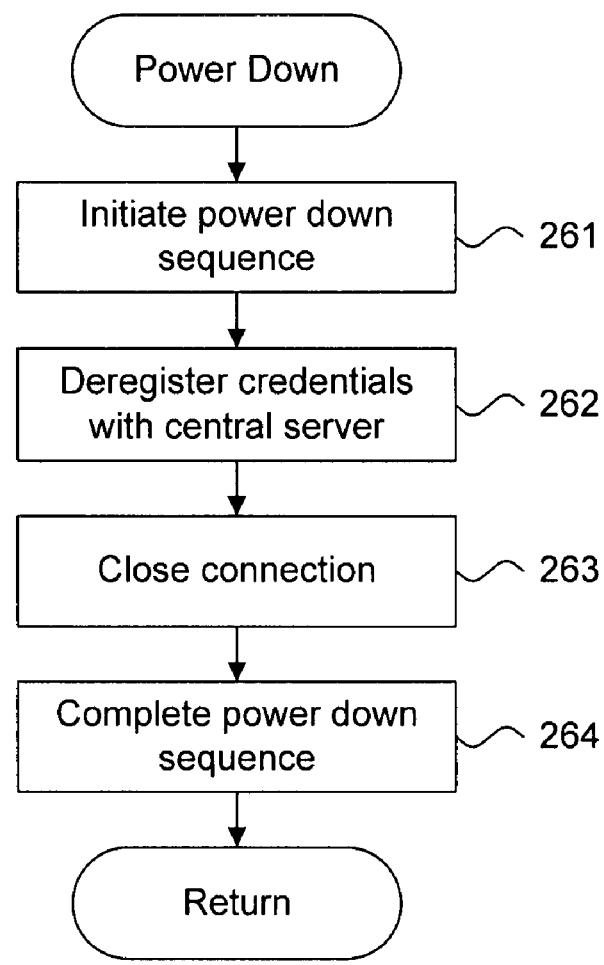
FIG. 10 is a flow diagram showing a routine for powering down for use in the routine of FIG. 6.

FIG. 10 is a flow diagram showing a routine 260 for powering down for use in the routine 200 of FIG. 6. The purpose of this routine is cleanly power down the programmer 141 while ensuring orderly deregistration with the security server 145.

The power down sequence of the programmer 141 is initiated (block 261). A high speed cellular connection 143 is initiated if necessary and the credentials 156 are deregistered with the security server 145 (block 262). The cellular connection 143 is then closed (block 263) and the power down sequence completes (block 264), after which the routine returns.

While the invention has been particularly shown and described as referenced to the embodiments thereof, those skilled in the art will understand that the foregoing and other changes in form and detail may be made therein without departing from the spirit and scope of the invention.

What is claimed is:

1. A physically secure programmer with atomic power up credentialing using a cellular network, comprising:
   a security certificate uniquely assigned by a security server and maintained in an internal memory;
   a cellular transceiver programmed to perform data exchange over a cellular network;
   boot sequence circuitry programmed to perform transparent and atomic power up credentialing with the security server, comprising:
      a security module programmed to provide the security certificate to the security server over a transient connection via the cellular transceiver, wherein the security server registers the security certificate against a roster of security certificates stored on the security server;
      a registration module programmed to await registration by the security server only if the transient connection was established; and
      one of an enabled status and a disabled status automatically assigned respectively following successful and unsuccessful registration of the security certificate;
   power up circuitry programmed to complete the atomic power up only if the enabled status is assigned and to terminate operation if the disabled status is assigned;
   a data exchange transceiver programmed to establish a data connection over the cellular network with at least one external device other than the security server subsequent to completion of the atomic power up;
   telemetry circuitry programmed to initiate and conduct a data exchange session via the cellular transceiver with at least one external device other than the security server subsequent to the completion of the atomic power up; and
   power down circuitry programmed to perform deregistration of the security certificate with the security server and to power down upon deregistration of the security certificate.

2. A programmer according to claim 1, further comprising:
   a transient wireless connection to interface to an implantable medical device, wherein a telemetric data exchange session is conducted with the implantable medical device.

3. A programmer according to claim 2, wherein the telemetric data exchange session comprises at least one of parametric values retrieval from the implantable medical device, patient history data retrieval from the implantable medical device and parametric values storage onto the implantable medical device.

4. A programmer according to claim 2, wherein the telemetric data exchange is conducted using at least one of induction and radio frequency telemetry.

5. A programmer according to claim 2, wherein the implantable medical device comprises at least one of an implantable cardiac device, neural stimulation device, and drug therapy dispensing device.

6. A programmer according to claim 1, wherein the security certificate is supplemented with credentials comprising at least one of a serial number and an asymmetric crypto key.

7. A programmer according to claim 1, wherein the security server maintains a set of programmer identifiers that each uniquely identify a programmer in association with a security credential, which is compared to register the programmer identifier matching the security certificate.

8. A programmer according to claim 7, wherein the programmer identifiers set signifies legitimate programmers, and a flag to signal the registration to confirm the operational status.

9. A programmer according to claim 7, wherein the programmer identifiers set signifies untrusted programmers, and a flag to signal a failure of the registration to deny the operational status.

10. A programmer according to claim 1, wherein the telemetry circuitry is further configured to interface to the at least one external device other than the security server, further comprising:
    an external device interface to initiate the data exchange session with the at least one interfaced external device other than the security server and to collaboratively exchange data with the at least one interfaced external device other than the security server.

11. A programmer according to claim 10, wherein the data exchange session comprises at least one of:
    at least one of parametric values, patient history data, control data, and general data downloaded from the at least one interfaced external device other than the security server; and
    at least one of parametric values, patient history data, control data, and general data stored onto the at least one interfaced external device other than the security server.

12. A programmer according to claim 10, wherein the at least one interfaced external device other than the security server further comprises a programmer and the external device interface is further configured to cooperatively exchange data relative to at least one implantable medical device having been interfaced to the programmer.

13. A programmer according to claim 10, wherein the at least one interfaced external device other than the security server further comprises a server, and analyzes data provided to the server by diagnosing a patient health status and prognosticating a clinical trajectory relative to the therapy to be delivered through an implantable medical device.

14. A programmer according to claim 1, further comprising:
    implementing at least one of a programmer recorder monitor, repeater, interrogator, recorder, monitor, and transceiver.

15. A programmer according to claim 1, wherein the at least one external device other than the security server comprises at least one of a server, client, programmer, printer, and repeater.

16. A method for providing atomic power up credentialing of a physically secure programmer using a cellular network, comprising:
    maintaining a security certificate uniquely assigned by a security server in an internal memory;
    performing data exchange over a cellular network;
    performing transparent and automatic power up credentialing with the security server, comprising:
       providing the security certificate to the security server over a transient connection via the cellular network, wherein the security server registers the security certificate against a roster of security certificates stored on the security server;
       awaiting registration by the security server only if the transient connection was established; and receiving one of an enabled status and a disabled status automatically assigned respectively following successful and unsuccessful registration of the security certificate;

completing the atomic power up only if the enabled status is assigned and terminating operation if the disabled status is assigned;

initiating and conducting a data exchange session via the cellular network with at least one external device other than the security server subsequent to the completion of the atomic power up; and performing deregistration of the security certificate with the security server and powering down upon deregistration of the security certificate.

17. A method according to claim 16, further comprising:
interfacing to an implantable medical device over a transient wireless connection; and
conducting a telemetric data exchange session with the implantable medical device.

18. A method according to claim 17, wherein the telemetric data exchange session comprises at least one of:
retrieving parametric values from the implantable medical device;
retrieving patient history data from the implantable medical device; and
storing parametric values onto the implantable medical device.

19. A method according to claim 17, wherein the telemetric data exchange is conducted using at least one of induction and radio frequency telemetry.

20. A method according to claim 17, wherein implantable medical device comprises at least one of an implantable cardiac device, neural stimulation device, and drug therapy dispensing device.

21. A method according to claim 16, wherein the security certificate is supplemented with credentials comprising at least one of a serial number and an asymmetric crypto key.

22. A method according to claim 16, further comprising:
maintaining a set of programmer identifiers on the security server that each uniquely identify a programmer in association with a security credential with is compared to register the programmer identifier matching the security certificate.

23. A method according to claim 22, wherein the programmer identifiers set signifies legitimate programmers, further comprising:
signaling the registration to confirm the operational status.

24. A method according to claim 22, wherein the programmer identifiers set signifies untrusted programmers, further comprising:
signaling the a failure of the registration to deny the operational status.

25. A method according to claim 16, further comprising:
interfacing to the at least one external device other than the security server;
initiating the data exchange session with the at least one interfaced external device other than the security server; and
collaboratively exchanging data with the at least one interfaced external device other than the security server.

26. A method according to claim 25, wherein the data exchange session comprises at least one of:
downloading at least one of parametric values, patient history data, control data, and general data from the at least one interfaced external device other than the security server; and
storing at least one of parametric values, patient history data, control data, and general data onto the at least one interfaced external device other than the security server.

27. A method according to claim 25, wherein the at least one interfaced external device other than the security server further comprises a programmer, further comprising:
cooperatively exchanging data relative to at least one implantable medical device having been interfaced to the programmer.

28. A method according to claim 25, wherein the at least one interfaced external device other than the security server further comprises a server, further comprising:
analyzing data provided to the server by diagnosing a patient health status and prognosticating a clinical trajectory relative to the therapy to be delivered through an implantable medical device.

29. A method according to claim 16, further comprising:
implementing at least one of a programmer recorder monitor, repeater, interrogator, recorder, monitor, and transceiver.

30. A method according to claim 16, wherein the at least one external device other than the security server comprises at least one of a server, client, programmer, printer, and repeater.

31. An apparatus for providing atomic power up credentialing of a physically secure programmer using a cellular network, comprising:
means for maintaining a security certificate uniquely assigned by a security server in an internal memory;
means for performing data exchange over a cellular network;
means for performing transparent and automatic power up credentialing with the security server, comprising:
means for providing the security certificate to the security server over a transient connection via the cellular network, wherein the security server registers the security certificate against a roster of security certificates stored on the security server;
means for awaiting registration by the security server only if the transient connection was established; and
means for receiving one of an enabled status and a disabled status automatically assigned respectively following successful and unsuccessful registration of the security certificate;
means for completing the atomic power up only if the enabled status is assigned and terminating operation if the disabled status is assigned; and
means for initiating and conducting a data exchange session via the cellular network with at least one external device other than the security server subsequent to the completion of the atomic power up; and
means for performing deregistration of the security certificate with the security server and powering down upon deregistration of the security certificate.

32. A physically secure programmer with atomic power up credentialing using a cellular network, comprising:
a security certificate uniquely assigned by a security server and maintained in an internal memory;
a cellular transceiver programmed to automatically establish first and second transient connections to the security server over a cellular network;
boot sequence circuitry programmed to perform transparent and atomic power up credentialing during the first transient connection, comprising:
a security module programmed to provide the security certificate to the security server via the cellular transceiver, wherein the security server registers the security certificate against a roster of security certificates stored on the security server that are uniquely assigned to only legitimate programmers;

a registration module programmed to await registration by the security server only if the first transient connection was established; and one of an enabled status and a disabled status automatically assigned respectively following successful and unsuccessful registration of the security certificate; and power up circuitry programmed to complete the atomic power up only after the enabled status is received;

a data exchange transceiver programmed to establish a data connection over the cellular network with at least one external device other than the security server subsequent to the completion of the atomic power up;

telemetry circuitry programmed to initiate and conduct a data exchange during the data connection; and power down circuitry programmed to perform deregistration with the security server during the second transient connection, comprising:

an initialization module programmed to initiate power down;

a deregistration module programmed to send a request to deregister the security certificate, wherein the security server deregisters the security certificate; and a finalization module programmed to complete power down.

33. A programmer according to claim 32, further comprising:

a transient wireless connection to interface to an implantable medical device, wherein a telemetric data exchange session is conducted with the implantable medical device.

34. A programmer according to claim 32, wherein the telemetry circuitry is further configured to interface to the at least one external device other than the security server, further comprising:

an external device interface to initiate the data exchange session with the at least one interfaced external device other than the security server and to collaboratively exchange data with the at least one interfaced external device other than the security server.

35. A method for providing atomic power up credentialing of a physically secure programmer using a cellular network, comprising:

maintaining a security certificate uniquely assigned by a security server in an internal memory;

automatically establishing first and second transient connections to the security server over a cellular network;

performing transparent and automatic power up credentialing with the security server during the first transient connection, comprising:

providing the security certificate to the security server via the cellular network, wherein the security server registers the security certificate against a roster of security certificates stored on the security server that are uniquely assigned to only legitimate programmers;

awaiting registration by the security server only if the first transient connection was established; and receiving one of an enabled status and a disabled status automatically assigned respectively following successful and unsuccessful registration of the security certificate;

completing the atomic power up only if the enabled status is received;

establishing a data connection with at least one external device other than the security server subsequent to the completion of the atomic power up over the cellular network;

initiating and conducting a data exchange session during the data connection;

performing deregistration with the security server during the second transient connection, comprising:

initiating power down;

sending a request to deregister the security certificate, wherein the security server deregisters the security certificate; and completing power down.

36. A method according to claim 35, further comprising:

interfacing to an implantable medical device over a transient wireless connection; and conducting a telemetric data exchange session with the implantable medical device.

37. A method according to claim 35, further comprising:

interfacing to the at least one external device other than the security server;

initiating the data exchange session with the at least one interfaced external device other than the security server; and collaboratively exchanging data with the at least one interfaced external device other than the security server.

* * * * *